(12) United States Patent
Moeckel et al.

(10) Patent No.: US 6,902,916 B2
(45) Date of Patent: Jun. 7, 2005

(54) NUCLEOTIDE SEQUENCES CODING FOR THE 1YSR1 GENE

(75) Inventors: Bettina Moeckel, Duesseldorf (DE); Mike Farwick, Bielefeld (DE); Thomas Hermann, Bielefeld (DE); Caroline Kreutzer, Melle (DE); Walter Pfefferle, Halle (DE)

(73) Assignee: Degussa AG, Düesseldorf (DE)

( * ) Notice: Subject to any disclaimer, the term of this patent is extended or adjusted under 35 U.S.C. 154(b) by 0 days.

(21) Appl. No.: 09/903,770

(22) Filed: Jul. 13, 2001

(65) Prior Publication Data

US 2003/0170780 A1 Sep. 11, 2003

(30) Foreign Application Priority Data

Aug. 10, 2000 (DE) .......................................... 100 39 044

(51) Int. Cl.[7] .............................................. C12P 13/08
(52) U.S. Cl. ...................... 435/115; 435/69.1; 435/106; 435/252.1; 435/252.3; 435/320.1; 536/23.1
(58) Field of Search ................................ 435/69.1, 106, 435/115, 252.1, 252.3, 320.1; 536/23.1

(56) References Cited

U.S. PATENT DOCUMENTS 6,210,951 B1    4/2001   Kawasaki et al.

FOREIGN PATENT DOCUMENTS

| EP | 1108790 A2 | 6/2001 |
| WO | WO 01/00802 | 1/2001 |
| WO | WO 01/00843 | 1/2001 |
| WO | WO 01/00845 | 1/2001 |
| WO | WO 01/00847 | 1/2001 |

OTHER PUBLICATIONS

Ventura et al. GenBank Accession AFO98867 (Alignment No. 1).*
Database EMBL Online, Accession No. AB003155, Jan. 16, 2000.
Database EMBL Online, Accession No. Y10499, Jan. 8, 1998.
Bernhard J. Eikmanns, et al., Antonie Van Leeuwenhoek, vol. 64, No. 2, pp. 145–163, "Molecular Aspects of Lysine, Threonine, and Isoleucine Biosynthesis in Corynebacterium Glutamicum", 1993.
Reinhard Kraemer, Journal of Biotechnology, vol. 45, No. 1, pp. 1–21, "Genetic and Physiological Approaches for the Production of Amino Acids", 1996.
Mark A. Schell, Molecular Biology of the LysR Family of Transcriptional Regulators, Annu. Rev. Microbiol. 1993, 47:597–626.

* cited by examiner

Primary Examiner—Ponnathapu Achutamurthy
Assistant Examiner—Christian L Fronda
(74) Attorney, Agent, or Firm—Oblon, Spivak, McClelland, Maier & Neustadt, P.C.

(57) ABSTRACT

The present invention relates to polynucleotides corresponding to the lysR1 gene and which encode a LysR1 transcriptional regulator, methods of producing L-amino acids, and methods of screening for polynucleotides which encode proteins having LysR1 transcriptional regulator activity.

22 Claims, 1 Drawing Sheet

Figur 1: Plasmidkarte von pCR2.1lysR1int
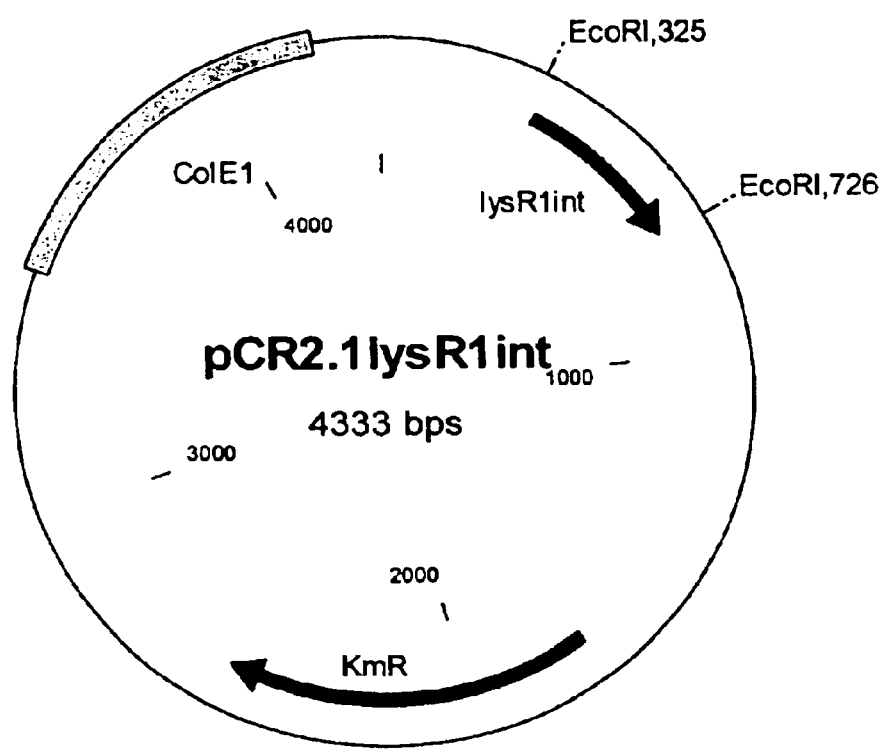

NUCLEOTIDE SEQUENCES CODING FOR THE 1YSR1 GENE

CROSS-REFERENCE TO RELATED APPLICATION

The present application claims priority to German Application No. DE 100 39 044.7 filed Aug. 10, 2000, the entire contents of which are incorporated herein by refeerence.

BACKGROUND OF THE INVENTION

1. Field of the Invention

The invention provides nucleotide sequences from Cozymeform bacteria which code for the lysR1 gene and a process for the fermentative preparation of amino acids, in particular L-lysine by attenuation of the lysR1 gene. The lysR1 gene codes for the LysR1 protein, which is a transcription regulator of the LysR family.

2. Discussion of the Background

L-amino acids, in particular L-lysine, are used in human medicine and in the pharmaceutical industry, in the foodstuffs industry, and most particularly in animal nutrition.

It is known that amino acids can be produced by fermentation of strains of Coryneform bacteria, in particular *Corynebacterium glutamicum*. On account of the great importance of these amino acids constant efforts are being made to improve the production processes. Improvements in production processes may involve fermentation technology measures, such as for example stirring and provision of oxygen, or the composition of the nutrient media, such as for example the sugar concentration during the fermentation, or the working up to the product form by for example ion exchange chromatography, or the intrinsic performance properties of the microorganism itself.

Methods involving mutagenesis, selection and mutant selection are used to improve the performance properties of these microorganisms. In this way strains are obtained that are resistant to antimetabolites or are auxotrophic for regulatorily significant metabolites and that produce amino acids.

Methods of recombinant DNA have also been employed for improving strains of *Corynebacterium* strains which produce L-amino acids.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of lysR1 gene encoding the a LysR1 transcriptional regulation protein would improve L-amino acid yields.

SUMMARY OF THE INVENTION

One object of the present invention, is providing a new process adjuvant for improving the fermentative production of L-amino acids, particularly L-lysine and L-glutamate. Such process adjuvants include enhanced bacteria, preferably enhanced Coryneform bacteria which express attenuated amounts of LysR1 transcriptional regulator which is encoded by the lysR1 gene.

Thus, another object of the present invention is providing such an bacterium, which expresses an attenuated amount of LysR1 transcriptional regulator or gene products of the lysR1 gene.

Another object of the present invention is providing a bacterium, preferably a Corynefoxm bacterium, which expresses a polypeptide that has an attenuated LysR1 transcriptional regulator activity.

Another object of the invention is to provide a nucleotide sequence encoding a polypeptide which has LysR1 transcriptional regulator sequence. One embodiment of such a sequence is the nucleotide sequence of SEQ ID NO: 1.

A further object of the invention is a method of making LysR3 transcriptional regulator or an isolated polypeptide having a LysR1 transcriptional regulator activity, as well as use of such isolated polypeptides in the production of In amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have LysR1 transcriptional regulator activity, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWING

FIG. 1: Map of the plasmid pCR2.1lysR1int.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

As used herein, L-amino acids or amino acids are understood to mean and amino acid or its salt. Preferably, the amnio acids are chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

As used herein L-lysine or lysine include not only the bases but also the salts, such as e.g. lysine monohydrochloride or lysine sulfate.

The invention provides an isolated polynucleotide of Coryneform bacteria containing a polynucleotide sequence coding for the lysR1 gene, selected from the group comprising a) polynucleotide that is at least 70% identical to a polynucleotide coding for a polypeptide that contains the amino acid sequence of SEQ ID No. 2, b) polynucleotide coding for a polypeptide that contains an amino acid sequence that is at least 70% identical to the amino acid sequence of SEQ ID No. 2, c) polynucleotide that is complementary to the polynucleotides of a) or b), and d) polynucleotide containing at least 15 successive nucleotides of the polynucleotide sequence of a), b) or c), the polypeptide preferably having the activity of the transcription regulator lysR1.

The invention also provides the aforementioned polynucleotide, which is preferably a replicable DNA containing:

(i) the nucleotide sequence shown in SEQ ID No.1, or (ii) at least one sequence that corresponds to the sequence (i) within the region of degeneration of the genetic code, or (iii) at least one sequence that hybridises with the sequences that are complementary to the sequences (i) or (ii), and optionally (iv) functionally neutral sense mutations in (i).

The invention furthermore provides:

a replicable DNA containing the nucleotide sequence as illustrated in SEQ ID No.1;

a polynucleotide coding for a polypeptide that contains the amino acid sequence as is illustrated in SEQ ID No. 2;

a vector containing the polynucleotide d) according to the invention, in particular pCR2.1lysR1int inserted into *E. Coli* DSM 13616 and filed at DSMZ, Brunswick, (Germany);

and Coryneform bacteria that in the lysR1 gene contain an insertion or deletion, in particular by using the vector pCR2.1lysR1int.

The invention thus provides polynucleotides consisting substantially of a polynucleotide sequence, that are obtainable by screening by hybridising a corresponding gene library that contains the complete gene with the polynucleotide sequence corresponding to SEQ ID No.1, with a probe that contains the sequence of the aforementioned polynucleotide according to SEQ ID No. 1 or a fragment thereof, and isolating the aforementioned DNA sequence.

Polynucleotide sequences according to the invention are suitable as hybridisation probes for RNA, cDNA and DNA, in order to isolate nucleic acids, polynucleotides or genes in their full length that code for lysR1 protein, or to isolate such nucleic acids or polynucleotides or genes that have a high degree of similarity to the sequence of the lysR1 gene.

Polynucleotide sequences according to the invention are further suitable as primers with the polymerase chain reaction (PCR), DNA of genes can be produced that code for lysR1 protein.

Such oligonucleotides serving as probes or primers contain at least 30, preferably at least 20, and most particularly preferably at least 15 successive nucleotides. Also suitable are oligonucleotides having a length of at least 40 or 50 nucleotides.

"Isolated" denotes separated from its natural environment.

"Polynucleotide" refers in general to polyribonucleotides and polydeoxyribonucleotides, which may either be unmodified RNA or DNA or modified RNA or DNA.

The term "polypeptides" denotes peptides or proteins that contain two or more amino acids bound via peptide bonds.

The polypeptides according to the invention include a polypeptide according to SEQ ID No. 2, in particular those peptides having the biological activity of lysR1 protein, and also those polypeptides that are at least 70%, preferably at least 80% and particularly preferably at least 90% to 95% identical to the polypeptide according to SEQ ID No. 2 and have the aforementioned activity.

The present invention furthermore relates to a process for the enzymatic production of amino acids, in particular L-lysine, using Coryneform bacteria that in particular already produce amino acids and in which the nucleotide sequences coding for the lysR1 gene are attenuated, in particular are switched off or are expressed at a low level.

The term "attenuation" used in this context denotes the reduction or switching off of the intracellular activity of one or more enzymes (proteins) in a microorganism that are coded by the corresponding DNA, by for example using a weak promoter or using a gene or allele that codes for a corresponding gene having a low activity or that inactivates the corresponding gene or enzyme (protein), and optionally combining these measures.

The microorganisms that are the subject of the present invention may produce amino acids, in particular L-lysine, from glucose, sucrose, lactose, fructose, maltose, molasses, starch, cellulose or from glycerol and ethanol. These microorganisms may be representatives of Coryneform bacteria, in particular of the genus *Corynebacterium*. In the genus *Corynebacterium* the species *Corynebacterium glutamicum* should in particular be mentioned, which is known to those skilled in the art for its ability to produce L-amino acids.

Suitable strains of the genus *Corynebacterium*, in particular of the species *Corynebacterium glutamicum* (*C. glutamicum*), are in particular the known wild type strains

*Corynebacterium glutamicum* ATCC13032

*Corynebacterium acetoglutamicum* ATCC15806

*Corynebacterium acetoacidophilum* ATCC13870

*Corynebacterium inelassecola* ATCC17965

*Corynebacterium thermoaminogenes* FERM BP-1539

*Brevibacteriurum flavum* ATCC14067

*Brevibacterium lactofermentum* ATCC13869 and

*Brevibacterium divaricatum* ATCC14020 or mutants or strains formed therefrom that produce L-amino acids, such as for example the strains producing L-lysine.

*Corynebacterium glutamicum* FERM-P 1709

*Brevibacterium flavum* FERM-P 1708

*Brevibacterium lactofermentun* FERM-P 1712

*Corynebacterium glutamicum* FERM-P 6463

*Corynebacterium glutamicurn* FERM-P 6464

*Corynebacterium glutamicum* DM58-1

*Corynebacterium glutamicum* DG52-5

*Corynebacterium glutamicum* DSM 5714 and

*Corynebacteriun glutamicum* DSM 12866

Preferably, a bacterial strain with attenuated expression of a lysR1 gene that encodes a polypeptide with LysR1 transcriptional regulation activity will improve amino acid yield at least 1%.

The inventors have successfully isolated the new lysR1 gene from *C. glutamicum* coding for lysR1 protein, which is a transcription regulator of the lysR family.

In order to isolate the lysR1 gene or also other genes from *C. glutamicum*, a gene library of this microorganism is hi first of all introduced into *Escherichia coli* (*E. coli*). The introduction of gene libraries is described in generally known textbooks and manuals. As an example there may be mentioned the textbook by Winnacker: Gene and Klone, Eine Einführung in die Gentechnologie (Verlag Chemie, Weinheim, Germany, 1990), or the manual by Sambrook et al.: Molecular Cloning, A Laboratory Manual (Cold Spring Harbor Laboratory Press, 1989). A very well-known gene library is that of the *E. coli* K-12 strain W3110, which was introduced by Kohara et al. (Cell 50, 495–508 (1987)) into λ-vectors. Bathe et al. (Molecular and General Genetics, 252:255–265, 1996) describe a gene library of *C. glutamicum* ATCC13032, which was introduced by means of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research. 16:1563–1575). Börmann et al. (Molecular Microbiology 6(3), 317–326 (1992)) again describe a gene library of *C. glutamicum* ATCC13032 using the cosmid pHC79 (Hohn and Collins, 1980, Gene 11, 291–298).

In order to produce a gene library of *C. glutamicum* in *E. coli* plasmids such as pBR322 (Bolivar, 1979, Life Sciences, 25, 807–818) or pUC9 (Vieira et al., 1982, Gene, 19:259–268) may also be employed. Suitable hosts are in particular those *E. coli* strains that are restriction and recombinant defective, for example the strain DH5α, (Jeffrey H. Miller: "A Short Course in Bacterial Genetics, A Laboratory Manual and Handbook for *Escherichia coli* and Related Bacteria", Cold Spring Harbor Laboratory Press, 1992)

The long DNA fragments cloned with the help of cosmids or other λ-vectors may then in turn be subcloned into conventional vectors suitable for DNA sequencing.

Methods of DNA sequencing are described in, inter alia, Sanger et al. (Proceedings of the National Academy of Sciences of the United States of America USA, 74:5463–5467, 1977).

The DNA sequences obtained may then be investigated with known algorithms or sequence analysis programs, such as for example that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* coding for the lysR1 gene was obtained in this way, and as SEQ ID No. 1 is part of the present invention. The amino acid sequence of the corresponding protein was also derived from the existing DNA sequence using the aforedescribed methods. The resulting amino acid sequence of the lysR1 gene product is shown in SEQ ID No. 2.

Coding DNA sequences that are obtained from SEQ ID No. 1 as a result of the degenerability of the genetic code are also covered by the invention. Similarly, DNA sequences that hybridise with SEQ ID No. 1 or parts of SEQ ID No. 1 are also covered by the invention. Furthermore, in this specialist field conservative aminoacid replacements, such as for example the replacement of glycine by alanine or of aspartic acid by glutamic acid in proteins, are known as sense mutations, which do not lead to any fundamental change in the activity of the protein, i.e. are functionally neutral. Furthermore, it is known that changes at the N-terminus and/or C-terminus of a protein do not significantly impair or may even stabilise its function. Those skilled in the art can find details of this in, inter alia, Ben-Bassat et al. (Journal of Bacteriology 169:751–757 (1987)), in O'Regan et al. (Gene 77:237–251 (1989)), in Sahiri-Toth et al. (Protein Sciences 3:240–247 (1994)), in Hochuli et al. (Bio/Technology 6:1321–1325 (1988)) and in known textbooks of genetics and molecular biology. Amino acid sequences that are obtained in a corresponding manner from SEQ ID No. 2 are likewise covered by the invention.

Finally, DNA sequences that are produced by the polymerase chain reaction (PCR) using primers resulting from SEQ ID No. 1, are also covered by the invention. Such oligonucleotides typically have a length of at least 15 nucleotides.

The person skilled in the art can find details of the identification of DNA sequences by means of hybridisation in, inter alia, the textbook "The DIG System User's Guide for Filter Hybridization" published by Boehringer Mannheim GmbH (Mannheim, Germany, 1993) and in Liebl et al. (International Journal of Systematic Bacteriology 41: 255–260 (1991)). The person skilled in the art can obtain details of the amplification of DNA sequences by means of the polymerase chain reaction (PCR) in, inter alia, the handbook by Gait: Oligonucleotide Synthesis: A Practical Approach (IRL Press, Oxford, UK, 1984) and the Newton and Graham: PCR (Spektrum Akademischer Verlag, Heidelberg, Germany, 1994).

In the course of work carried out on the present invention it was found that Coryneform bacteria after attenuation of the lysR1 gene produce amino acids, in particular L-lysine, in an improved manner.

In order to achieve an attenuation, either the expression of the lysR1 gene or the catalytic properties of the enzyme protein may be reduced or switched off. Optionally both measures may be combined.

The reduction of the gene expression may be achieved by suitable culture conditions or by genetic alteration (mutation) of the signal structures of the gene expression. Signal structures of the gene expression are for example repressor genes, activator genes, operators, promoters, attenuators, ribosome binding sites, the start codon and terminators. The person skilled in the art can obtain further information on this in for example patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as for example the textbook by Knippers ("Molekulare Genetik", 6$^{th}$ Edition, Georg Thieme Verlag, Stuttgart, Germany, 1995) or the textbook by Winnacker ("Gene and Klone", VCH Verlagsgesellschaft, Weinheim, Germany, 1990).

Mutations that lead to an alteration or reduction of the catalytic properties of enzyme proteins are known in the prior art; as examples there may be mentioned the work of Qiu and Goodman (Journal of Biological Chemistry 272: 8611–8617 (1997)), Sugimoto et al. (Bioscience Biotechnology and Biochemistry 61: 1760–1762 (1997)) and Mockel ("Die Threonindehydratase aus *Corynebacterium glutamicum*: Aufhebung der allosterischen Regulation and Struktur des Enzyms", and reports published by the Jülich Research Centre, Jül-2906, ISSN09442952, Jülich, Germany, 1994). Overviews may be obtained from known textbooks on genetics and molecular biology, for example that of Hagemann ("Allgemeine Genetik", Gustav Fischer Verlag, Stuttgart, 1986).

Mutations in the present context include transitions, transversions, insertions and deletions. Depending on the effect of the amino acid replacement on the enzyme activity, one talks either of missense mutations or nonsense mutations. Insertions or deletions of at least one base pair (bp) in a gene lead to frame shift mutations, following which false amino acids are incorporated or the translation terminates prematurely. Deletions of several codons typically lead to a complete cessation of enzyme activity. Details of the production of such mutations are part of the priorart and may be obtained from known textbooks on genetics and molecular biology, such as for example the textbook by Knippers ("Molekulare Genetik", 6$^{th}$ Edition, Georg Thieme Verlag, Stuttgart, Germany, 1995), the textbook by Winnacker ("Gene and Klone", VCH Verlagsgesellschaft, Weinheim, Germany, 1990) or the textbook by Hagemann ("Allgemeine Genetik", Gustav Fischer Verlag, Stuttgart, 1986).

A conventional method of mutating genes of *C. glutamicum* is the method of gene disruption and gene replacement described by Schwarzer and Pühler (Bio/Technology 9, 84–87 (1991)).

In the method of gene disruption a central part of the coding region of the gene in question is cloned into a plasmid vector that can replicate in a host (typically *E. coli*), but not in *C. glutamicum*. Suitable vectors are for example pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega Corporation, Madison, Wis., USA), pCR2.1-TOPO (Shuman (1994), Journal of Biological Chemistry 269:32678–84; U.S. Pat. No. 5,487,993), pCR®Blunt (Invitrogen, Groningen, Netherlands; Bernard et al., Journal of Molecular Biology, 234: 534–541 (1993)) or pEM1 (Schrumpf et al, 1991, Journal of Bacteriology 173:4510–4516). The plasmid vector that contains the central part of the coding region of the gene is then converted by conjugation or transformation into the desired strain of *C. glutamicum*. The method of conjugation is described for example by Schäfer et al. (Applied and Environmental Microbiology 60, 756–759 (1994)). Methods of transformation are described for example in Thierbach et al. (Applied Microbiology and Biotechnology 29, 356–362 (1988)), Dunican and Shivnan (Bio/Technology 7, 1067–1070 (1989)) and Tauch et al. (FEMS Microbiological. Letters 123, 343–347 (1994)). After homologous recombination by means of a cross-over event, the coding region of the relevant gene is disrupted by the vector sequence and two incomplete alleles are obtained, missing respectively the 3'- and 5'-end. This method has been used for example by Fitzpatrick et al. (Applied Microbiology and Biotechnology 42, 575–580 (1994)) to switch off the recA gene of *C. glutamicum*.

FIG. 1 shows for example the plasmid vector pCR2.1 lysR1int, by means of which the lysR1gene can be disrupted or switched off.

In the gene replacement method a mutation, such as for example a deletion, insertion or base replacement, is produced in vitro in the gene that is of interest. The resultant allele is in turn cloned into a non-replicative vector for *C. glutamicum*, and this is then converted by transformation or conjugation into the desired host of *C. glutamicum*. After homologous recombination by means of a first cross-over event effecting integration, and an appropriate second cross-over event effecting an excision, the incorporation of the mutation or allele in the target gene or in the target sequence is achieved. This method has been used for example by Peters-Wendisch et al. (Microbiology 144, 915–927 (1998)) to switch off the pyc gene of *C. glutamicum* by a deletion.

A deletion, insertion or a base replacement can be incorporated into the lysR1 gene in this way.

In addition, it may be advantageous for the production of L-amino acids, in particular L-lysine, in addition to the attenuation of the lysR1 gene, also to enhance, in particular overexpress, one or more enzymes of the respective biosynthesis pathway, glycolysis, anapleurosis, pentose phosphate cycle, or amino acid export.

Thus for example, for the production of L-lysine one or more of the genes selected from the following group may simultaneously be enhanced, in particular overexpressed the gene dapA coding for dihydrodipicolinate synthase (EP-B 0 197 335), the gene eno coding for enolase (DE: 19947791.4), the gene zwf coding for the zwf gene product (JP-A-25 09224661), the gene pyc coding for pyruvate carboxylase (Peters-Wendisch et al. (Microbiology 144, 915–927 (1998))

the gene lysE coding for lysine export (DE-A-195 48 222).

Also, it may be advantageous for the production of amino acids, especially L-lysine, besides attenuating the lysR1 gene, at the same time to attenuate one or more of the genes selected from the group the gene pck coding for phosphoenol pyruvate carboxykinase (DE 199 50 409.1, DSM 13047), the gene pgi coding for glucose-6-phosphate isomerase (U.S. Ser. No. 09/396,478, DSM 12969), the gene poxB coding for pyruvate oxidase (DE:1995 1975.7, DSM 13114)

Moreover, it may be advantageous for the production of amino acids, in particular L-lysine, in addition to attenuating the lysR1 gene also to switch off undesirable secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention are likewise covered by the invention and for the purposes of producing L-amino acids, in particular L-lysine, may be cultivated continuously or batchwise in a batch process, or in a feed batch process or repeated batch process. A summary of known cultivation methods is described in the textbook by Chmiel (Bioprozesstechnik 1. Einführung in die Bioverfahrens-technik (Gustav Fischer Verlag, Stuttgart, 1991)) or in the textbook by Storhas (Bioreaktoren und periphere Einrichtungen (Vieweg Verlag, Brunswick/Wiesbaden, 1994)).

The culture medium to be used must satisfy in an appropriate manner the requirements of the respective strains. Descriptions of culture media for various microorganisms are given in the handbook "Manual of Methods. for General Bacteriology" of the American Society for Bacteriology (Washington D.C., USA, 1981). As carbon source there may be used sugars and carbohydrates such as for example glucose, sucrose, lactose, fructose, maltose, molasses, starch and cellulose, oils and fats such as for example soya oil, sunflower oil, groundnut oil and coconut oil, fatty acids such as for example palmitic acid, stearic acid and linoleic acid, alcohols such as for example glycerol and ethanol, and organic acids such as for example acetic acid. These substances may be used individually or as a mixture.

As nitrogen source there may be used organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources may be used individually or as a mixture.

As phosphorus source there may be used phosphoric acid, potassium dihydrogen phosphate or dipotassium hydrogen phosphate, or the corresponding sodium-containing salts. The culture medium must furthermore contain salts of metals, such as for example magnesium sulfate or iron sulfate, that are necessary for growth. Finally, essential growth promoters such as amino acids and vitamins may in addition be added to the aforementioned substances. Suitable precursors may moreover be added to the culture medium. The aforementioned starting substances may be added to the culture in the form of a single batch, or metered in in an appropriate manner during the cultivation procedure.

In order to control the pH of the culture basic compounds such as sodium hydroxide, potassium hydroxide, ammonia or ammonia water, or acidic compounds such as phosphoric acid or sulfuric acid may be added in an appropriate manner. In order to control foam formation anti-foaming agents such as for example fatty acid polyglycol esters may be used. In order to maintain the stability of plasmids selectively acting substances, such as for example antibiotics, may be added to the medium. In order to maintain aerobic conditions, oxygen or oxygen-containing gas mixtures, such as for example air, are pumped into the culture. The temperature of the culture is normally 20° C. to 45° C. and preferably 25° C. to 40° C. The cultivation is continued until a maximum amount of the desired product has been formed. This target is normally reached within 10 hours to 160 hours.

Methods for determining L-amino acids are known from the prior art. The analysis may for example be carried out as described by Spackman et al. (Analytical Chemistry, 30, (1958), 1190) by anion exchange chromatography followed by ninhydrin derivatisation, or it may be carried out by reversed phase HPLC, as described by Lindroth et al. (Analytical Chemistry (1979) 51: 1167–1174).

The following microorganism has been filed according to the Budapest Convention at the German Collection for Microorganisms and Cell Cultures (DSMZ, Brunswick, Germany).

*Escherichia coli* strain *E. coli* TOP10F/pCR2.1lysR1int as DSM 13616.

The process according to the invention serves for the enzymatic production of amino acids, in particular L-lysine.

The present invention is illustrated in more detail hereinafter with the aid of examples of implementation.

The isolation of plasmid DNA from *Escherichia coli* as well as all techniques for the restriction, Klenow and alkaline phosphatase treatment were carried out according to Sambrook et al. (Molecular Cloning. A Laboratory Manual, 1989, Cold Spring Harbour Laboratory Press, Cold Spring Harbor, N.Y., USA). Methods for the transformation of *Escherichia coli* are likewise described in this handbook.

The compositions of conventional nutrient media such as LB medium or TY medium may also be obtained from the handbook by Sambrook et al., Molecular Cloning: A Laboratory Manual, Cold Spring Harbor Laboratory, New York (1989).

EXAMPLE 1

Production of a genomic cosmid gene library from *C. glutamicum* ATCC 13032

Chromosomal DNA from *C. glutainicum* ATCC 13032 was isolated as described by Tauch et al., (1995, Plasmid 33:168–179) and partially cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164), obtained from Stratagene (La Jolla, USA, Product Description SuperCosl Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this way was mixed with the treated ATCC13032-DNA, and the batch was then treated with T4-DNA ligase (Amersham Pharmacia, Freiburg, Germany, Product Description T4-DNA ligase, Code no.27-0870-04). The ligation mixture was then packed into phages using Gigapack II XL Packing Extracts (Stratagene, La Jolla, USA, Product Description Gigapack II XL Packing Extract, Code no. 200217).

In order to infect the *E. coli* strain NM554 (Raleigh et al. 1988, Nucleic Acid Res. 16:1563–1575) the cells were taken up in 10 mM $MgSO_4$ and mixed with an aliquot of the phage suspension. Infection and titration of the cosmid library were carried out as described by Sambrook et al. (1989, Molecular Cloning: A Laboratory Manual, Cold Spring Harbor), the cells being plated out on LB agar (Lennox, 1955, Virology, 1:190)+100 µg/ml ampicillin. After incubation overnight at 37° C. recombinant individual clones were selected.

EXAMPLE 2

Isolation and sequencing of the Gene LysR1

The cosmid DNA of an individual colony was isolated with the Qiaprep Spin Miniprep Kit (Product No. 27106, Qiagen, Hilden, Germany) according to the manufacturer's instructions and then partially cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After gel electrophoresis separation the cosmid fragments were isolated in the size range from 1500 to 2000 bpusing the QiaExII Gel Extraction Kit (Product No. 20021, Qiagen, Hilden, Germany).

The DNA of the sequencing vector pZero-1 obtained from Invitrogen (Groningen, Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments into the sequencing vector pZero-1 was carried out as described by Sambrook et al. (1989, Molecular Cloning: A Laboratory Manual, Cold Spring Harbor), the DNA mixture having been incubated overnight with T4 ligase (Pharmacia Biotech, Freiburg, Germany). This ligation mixture was then electroporated into the *E. coli* strain DH5 MCR (Grant, 1990, Proceedings of the National Academy of Sciences, U.S.A., 87:4645–4649) (Tauch et al. 1994, FEMS Microbiol. Letters, 123:343–7) and plated out onto LB-agar (Lennox, 1955, Virology, 1:190) with 50 µg/l zeocin.

The plasmid preparation of the recombinant clone was carried out with the Biorobot 9600 (Product No. 900200, Qiagen, Hilden, Germany). The sequencing was performed according to the dideoxy chain termination method of Sanger et al. (1977, Proceedings of the National Academies of Sciences, U.S.A., 74:5463–5467) as modified by Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The gel electrophoresis separation and analysis of the sequencing reaction were carried out in a "Rotiphoresis NF Acrylamide/Bisacrylamide" Gel (29:1) (Product No. A124.1, Roth, Karlsruhe, Germany) using the "ABI Prism 377" sequencing device from PE Applied Biosystems (Weiterstadt, Germany).

The raw sequence data thus obtained were then processed using the Staden Program Package (1986, Nucleic Acids Research, 14:217–231) Version 97-0. The individual sequences of the pzerol derivates were assembled to form a coherent contig. The computer-assisted coding region analysis was prepared using the XNIP program (Staden, 1986, Nucleic Acids Research, 14:217–231). Further analyses were carried out with the "BLAST search programs" (Altschul et al., 1997, Nucleic Acids Research, 25:33893402) against the non-redundant database of the National Center for Biotechnology Information (NCBI, Bethesda, Md., USA).

The nucleotide sequence thus obtained is represented in SEQ ID No. 1. Analysis of the nucleotide sequence revealed an open reading frame of 912 base pairs, which was termed the lysR1 gene. The lysR1 gene codes for a polypeptide of 304 amino acids.

EXAMPLE 3

Production of an Integration Vector for the Integration Mutagenesis of the LysR1 gene Chromosomal DNA was isolated from the strain ATCC 13032 by the method of Eikmanns et al. (Microbiology 140: 1817–1828 (1994)). On account of the sequence of the lysR1 gene known from Example 2 for *C. glutamicum*, the following oligonucleotides were selected for the polymerase chain reaction:

```
lysR1intA:
5' TTC CAA TCC CTG CTG TTC AC 3'    (SEQ ID NO:4)

lysR1intB:
5' GTG ACC TTT GAA ACC AGC GA 3'    (SEQ ID NO:5)
```

The represented primers were synthesised by MWG Biotech (Ebersberg, Germany) and the PCR reaction was carried out according to the standard PCR method of Innis et al. (PCR protocols. A guide to methods and applications, 1990, Academic Press) using Pwo polymerase from Boehringer. By means of the polymerase chain reaction a 383 bp long internal fragment of the lysR1 gene was isolated, which is shown in SEQ ID No. 3.

The amplified DNA fragment was ligated into the vector pCR2.1-TOPO (Mead at al. (1991) Bio/Technology 9:657–663) using the TOPO TA Cloning Kit from Invitrogen Corporation (Carlsbad, Calif., USA; Cat. No. K4500-01).

The *E. coli* strain TOP10F was then transformed with the ligation batch (Hanahan, In: DNA cloning. A practical approach. Vol. I. IRL-Press, Oxford, Washington DC, USA, 1985). Plasmid-carrying cells were selected by plating out the transformation batch onto LB agar (Sambrook et al., Molecular cloning: a laboratory manual. 2$^{nd}$ Ed. Cold Spring Harbor Laboratory Press, Cold Spring Harbor, N.Y., 1989) that had been supplemented with 25 mg/l of kanamycin. Plasmid DNA was isolated from a transformant using the QIAprep Spin Miniprep Kit from Qiagen and was checked by restriction with the restriction enzyme EcoRI followed by agarose gel electrophoresis (0.8%). The plasmid was named pCR2.1lysR1int.

EXAMPLE 4

Integration Mutagenesis of the LysR1 Gene in the Lysine Producer DSM 5715

The vector pCR2.1lysR1int mentioned in Example 3 was electroporated into *Corynebacterium glutamicum* DSM 5715 according to the electroporation method of Tauch et. al.(FEMS Microbiological Letters, 123:343–347 (1994)). The strain DSM 5715 is an AEC-resistant lysine producer. The vector pCR2.1lysR1int cannot replicate independently in DSM 5715 and thus only remains in the cell if it has integrated into the chromosome of DSM 5715. The selection of clones with pCR2.1lysR1int integrated into the chromosome was made by plating out the electroporation batch onto LB agar (Sambrook et al., Molecular cloning: a laboratory manual. 2$^{nd}$ Ed. Cold Spring Harbor Laboratory Press, Cold Spring Harbor, N.Y.) that had been supplemented with 15 mg/l of kanamycin.

In order to demonstrate the integration the lysR1int fragment was labelled using the Dig Hybridisation Kit from Boehringer according to the method described in "The DIG System User's Guide for Filter Hybridization" published by Boehringer Mannheim GmbH (Mannheim, Germany, 1993). Chromosomal DNA of a potential integrant was isolated according to the method of Eikmanns et al. (Microbiology 140: 1817–1828 (1994)) and was in each case cleaved with the restriction enzymes SalI, SacI and HindIII. The resultant fragments were separated by means of agarose gel electrophoresis and hybridised at 68° C. using the Dig Hybridisation Kit from Boehringer. The plasmid pCR2.1lysR1int mentioned in Example 3 had inserted itself into the chromosome of DSM 5715 within the chromosomal lysR1 gene. The strain was designated DSM 5715::pCR2.1lysR1int.

EXAMPLE 5

Production of Lysine

The *C. glutamicum* strain DSM 5715::pCR2.1lysR1int obtained in Example 4 was cultivated in a nutrient medium suitable for the production of lysine and the lysine content in the culture supernatant was determined.

For this purpose the strain was first of all incubated for 24 hours at 33° C. on an agar plate with the corresponding antibiotic (brain-heart agar with kanamycin (25 mg/l). Starting from this agar plate culture a preculture was inoculated (10 ml of medium in a 100 ml Erlenmeyer flask). The full medium CgIII was used as medium for the preculture.

| Medium Cg III | |
| --- | --- |
| NaCl | 2.5 g/l |
| Bacto-Peptone | 10 g/l |
| Bacto-Yeast Extract | 10 g/l |
| Glucose (autoclaved separately) | 2% (w/v) |

The pH value was adjusted to pH 7.4

Kanamycin (25 mg/l) was added to this preculture. The preculture was then incubated for 24 hours at 33° C. at 240 rpm on a shaker table. From this preculture a main culture was inoculated so that the initial OD (660 nm) of the main culture was 0.1 OD. The medium MM was used for the main culture.

| Medium MM | |
| --- | --- |
| CSL (Corn Steep Liquor) | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 \cdot 7H_2O$ | 1.0 g/l |
| $CaCl_2 \cdot 2H_2O$ | 10 mg/l |
| $FeSO_4 \cdot 7H_2O$ | 10 mg/l |

-continued

| Medium MM | |
|---|---|
| MnSO$_4$.H$_2$O | 5.0 mg/l |
| Biotin (sterile filtered) | 0.3 mg/l |
| Thiamine.HCl (sterile filtered) | 0.2 mg/l |
| Leucine (sterile filtered) | 0.1 g/l |
| CaCO$_3$ | 25 g/l |

CSL, MOPS and the salt solution are adjusted with ammonia water to pH 7 and autoclaved. The sterile substrate and vitamin solutions as well as the dry autoclaved CaCO$_3$ are then added.

Cultivation is carried out in a 10 ml volume in a 100 ml Erlenmeyer flask equipped with baffles. Kanamycin was added (25 mg/l). The cultivation was carried out at 33° C. and 80% atmospheric humidity.

After 72 hours the OD was determined at a measurement wavelength of 660 nm with a Biomek 1000 (Beckmann Instruments GmbH, Munich). The amount of lysine formed was determined by ion exchange chromatography and post-column derivatisation with ninhydrin detection using an amino acid analyser from Eppendorf-BioTronik (Hamburg, Germany).

The results of the experiment are shown in Table 1.

TABLE 1

| Strain | OD(660) | Lysine-HCl g/l |
|---|---|---|
| DSM 5715 | 7.5 | 13.01 |
| DSM 5715:: pCR2.1lysR1int | 7.7 | 15.64 |

The acronyms and abbreviations used have the following meanings.
KFNR: Kanamycin resistance gene
EcoRI: Cleavage site of the restriction enzyme EcoRI
lysR1int: Internal fragment of the lysR1 gene
ColE1 ori: Replication origin of the plasmid ColE1

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide from *Corynebacterium* which encodes a protein comprising the amino acid sequence of SEQ ID NO: 2.

2. The polynucleotide of claim 1, which comprises nucleotides 201 to 1109 of SEQ ID NO: 1.

3. The polynucleotide of claim 1, which is SEQ ID NO: 1.

4. A vector comprising the polynucleotide of claim 1.

5. A microorganism transformed with the vector of claim 4.

6. A method of producing a protein which has the amino acid sequence of SEQ ID NO: 2, comprising culturing the transformed microorganism of claim 5 under conditions suitable to produce the protein and isolating the produced protein.

7. An isolated polynucleotide from *Corynebacterium glutamicum* which hybridizes under stringent conditions to SEQ ID NO: 1 or the full complement of SEQ ID NO: 1, wherein the stringent conditions comprise washing in 0.5× SSC at a temperature of 68° C., and wherein the polynucleotide encodes a protein that inhibits lysine production in a bacterial cell.

8. A vector comprising the polynucleotide of claim 7.

9. A microorganism transformed with the vector of claim 8.

10. A method of producing a protein which has the activity of inhibiting lysine production in a bacterial cell, comprising culturing the transformed microorganism of claim 9 under conditions suitable to produce the protein and purifying the produced protein.

11. An isolated polynucleotide consisting of 30 to 383 consecutive nucleotides of SEQ ID NO: 1.

12. An isolated polynucleotide consisting of at least 30 consecutive nucleotides of SEQ ID NO: 1.

13. The polynucleotide of claim 12, which is SEQ ID NO: 3.

14. A vector comprising the polynucleotide of claim 12.

15. The vector of claim 14, wherein the polynucleotide is SEQ ID NO: 3.

16. The vector of claim 14, which is pCR2.1lysR1int shown in FIG. 1 and deposited as DSM 13616 at the German Collection for Microorganisms and Cell Cultures (DSMZ, Brunswick, Germany).

17. *Escherichia coli* DSM 13616.

18. A process for producing L-amino acids, comprising culturing the *Escherichia coli* of claim 17 in a medium suitable for producing L-amino acids and collecting the L-amino acids produced.

19. The process of claim 18, wherein said Lamino acid is L-lysine.

20. The process of claim 18, wherein said L-amino acid is L-valine.

21. An isolated polynucleotide which comprises the full complement of nucleotides 201–1109 of SEQ ID NO: 1.

22. An isolated polynucleotide, which comprises the full complement of SEQ ID NO: 1.

\* \* \* \* \*

SEQUENCE LISTING

<160> NUMBER OF SEQ ID NOS: 5

<210> SEQ ID NO 1
<211> LENGTH: 1311
<212> TYPE: DNA
<213> ORGANISM: Corynebacterium glutamicum
<220> FEATURE:
<221> NAME/KEY: CDS
<222> LOCATION: (201)..(1109)
<223> OTHER INFORMATION:

<400> SEQUENCE: 1

```
acagcccagg ggccgttgag ggggaaaagc tgcgttccaa tggcagcacc aaattgcagg      60
gatagggcgg aacccatcac catcaacact gcagcggact gtttattcat gcccttgatt     120
attgccaaag aaacctttaa ggactagatc gaaaaacagc caactatagt taagtaatac     180
tgaacaattt tggaggtgtc gtg ctc aat ctc aac cgc tta cac atc ctg cag    233
                      Val Leu Asn Leu Asn Arg Leu His Ile Leu Gln
                        1               5                  10 gaa ttc cac cgc ctg gga acg att aca gca gtg gcg gaa tcc atg aac     281
Glu Phe His Arg Leu Gly Thr Ile Thr Ala Val Ala Glu Ser Met Asn
             15                  20                  25 tac agc cgc tct gcc atc tcc caa caa atg gcg ctg ctg gaa aaa gaa     329
Tyr Ser Arg Ser Ala Ile Ser Gln Gln Met Ala Leu Leu Glu Lys Glu
         30                  35                  40 att ggt gtg aaa ctc ttt gaa aaa agc ggc cga aac ctc tac ttc aca     377
Ile Gly Val Lys Leu Phe Glu Lys Ser Gly Arg Asn Leu Tyr Phe Thr
     45                  50                  55 gaa caa ggc gaa gtg ttg gcc tca gaa aca cat gcg atc atg gca gca     425
Glu Gln Gly Glu Val Leu Ala Ser Glu Thr His Ala Ile Met Ala Ala
 60                  65                  70                  75 gtc gac cat gcc cgc gca gcc gtt cta gat tcg ctg tct gaa gtg tcc     473
Val Asp His Ala Arg Ala Ala Val Leu Asp Ser Leu Ser Glu Val Ser
                 80                  85                  90 gga acg ctg aaa gtc acc tcc ttc caa tcc ctg ctg ttc acc ctt gcc     521
Gly Thr Leu Lys Val Thr Ser Phe Gln Ser Leu Leu Phe Thr Leu Ala
             95                 100                 105
```

-continued

```
ccg aaa gcc atc gcg cgc ctg acc gag aaa tac cca cac ctg caa gta      569
Pro Lys Ala Ile Ala Arg Leu Thr Glu Lys Tyr Pro His Leu Gln Val
        110                 115                 120 gaa atc tcc caa cta gaa gtc acc gca gcg ctc gaa gaa ctc cgc gcc      617
Glu Ile Ser Gln Leu Glu Val Thr Ala Ala Leu Glu Glu Leu Arg Ala
    125                 130                 135 cgc cgc gtc gac gtc gca ctc ggc gag gaa tac ccc gtg gaa gtc ccc      665
Arg Arg Val Asp Val Ala Leu Gly Glu Glu Tyr Pro Val Glu Val Pro
140                 145                 150                 155 ctt gtt gag gcc agc att cac cgc gaa gtc ctc ttc gaa gac ccc atg      713
Leu Val Glu Ala Ser Ile His Arg Glu Val Leu Phe Glu Asp Pro Met
                160                 165                 170 ctg ctc gtc acc cca gca agc ggc cca tac tct ggc ctc acc ctg cca      761
Leu Leu Val Thr Pro Ala Ser Gly Pro Tyr Ser Gly Leu Thr Leu Pro
            175                 180                 185 gaa ctc cgc gac atc ccc atc gcc atc gat cca ccc gac ctt ccc gcg      809
Glu Leu Arg Asp Ile Pro Ile Ala Ile Asp Pro Pro Asp Leu Pro Ala
        190                 195                 200 ggc gaa tgg gtc cat agg ctc tgc cgg cgc gcc ggg ttt gag ccc cgc      857
Gly Glu Trp Val His Arg Leu Cys Arg Arg Ala Gly Phe Glu Pro Arg
    205                 210                 215 gtg acc ttt gaa acc agc gat ccc atg ctc caa gca cac ctc gtg cgt      905
Val Thr Phe Glu Thr Ser Asp Pro Met Leu Gln Ala His Leu Val Arg
220                 225                 230                 235 agc ggc ttg gcc gtg aca ttt tcc ccc aca ctg ctc acc ccg atg ctg      953
Ser Gly Leu Ala Val Thr Phe Ser Pro Thr Leu Leu Thr Pro Met Leu
                240                 245                 250 gaa agc gtg cac atc cag ccg ctg ccc ggc aac ccc acg cgc acg ctc     1001
Glu Ser Val His Ile Gln Pro Leu Pro Gly Asn Pro Thr Arg Thr Leu
            255                 260                 265 tac acc gcg gtc agg gaa ggg cgc cag ggg cat cca gcc att aaa gct     1049
Tyr Thr Ala Val Arg Glu Gly Arg Gln Gly His Pro Ala Ile Lys Ala
        270                 275                 280 ttt cga cga gcc ctc gcc cat gtg gcc aaa gaa tct tat ttg gag gct     1097
Phe Arg Arg Ala Leu Ala His Val Ala Lys Glu Ser Tyr Leu Glu Ala
    285                 290                 295 cgt cta gta gag tgagttcttg tgagccttca gacaaatcat cgcccagtac        1149
Arg Leu Val Glu
300 tcgtcgttga cttcggcgca cagtacgcgc agctgatcgc acgtcgtgtg cgtgaggccg   1209 gcatctactc cgaagtcatc ccgcacaccg ccaccgcaga cgatgtgcgc gctaaaaatg   1269 cagcagccct cgtcctttcc ggtggcccat cctccgtgta tg                     1311
```

<210> SEQ ID NO 2
<211> LENGTH: 303
<212> TYPE: PRT
<213> ORGANISM: Corynebacterium glutamicum

<400> SEQUENCE: 2

```
Val Leu Asn Leu Asn Arg Leu His Ile Leu Gln Glu Phe His Arg Leu
1               5                   10                  15

Gly Thr Ile Thr Ala Val Ala Glu Ser Met Asn Tyr Ser Arg Ser Ala
            20                  25                  30

Ile Ser Gln Gln Met Ala Leu Leu Glu Lys Glu Ile Gly Val Lys Leu
        35                  40                  45

Phe Glu Lys Ser Gly Arg Asn Leu Tyr Phe Thr Glu Gln Gly Glu Val
    50                  55                  60
```

```
Leu Ala Ser Glu Thr His Ala Ile Met Ala Ala Val Asp His Ala Arg
 65                  70                  75                  80

Ala Ala Val Leu Asp Ser Leu Ser Glu Val Ser Gly Thr Leu Lys Val
                 85                  90                  95

Thr Ser Phe Gln Ser Leu Leu Phe Thr Leu Ala Pro Lys Ala Ile Ala
            100                 105                 110

Arg Leu Thr Glu Lys Tyr Pro His Leu Gln Val Glu Ile Ser Gln Leu
        115                 120                 125

Glu Val Thr Ala Ala Leu Glu Glu Leu Arg Ala Arg Arg Val Asp Val
    130                 135                 140

Ala Leu Gly Glu Glu Tyr Pro Val Glu Val Pro Leu Val Glu Ala Ser
145                 150                 155                 160

Ile His Arg Glu Val Leu Phe Glu Asp Pro Met Leu Leu Val Thr Pro
                165                 170                 175

Ala Ser Gly Pro Tyr Ser Gly Leu Thr Leu Pro Glu Leu Arg Asp Ile
            180                 185                 190

Pro Ile Ala Ile Asp Pro Pro Asp Leu Pro Ala Gly Glu Trp Val His
        195                 200                 205

Arg Leu Cys Arg Arg Ala Gly Phe Glu Pro Arg Val Thr Phe Glu Thr
    210                 215                 220

Ser Asp Pro Met Leu Gln Ala His Leu Val Arg Ser Gly Leu Ala Val
225                 230                 235                 240

Thr Phe Ser Pro Thr Leu Leu Thr Pro Met Leu Glu Ser Val His Ile
                245                 250                 255

Gln Pro Leu Pro Gly Asn Pro Thr Arg Thr Leu Tyr Thr Ala Val Arg
            260                 265                 270

Glu Gly Arg Gln Gly His Pro Ala Ile Lys Ala Phe Arg Arg Ala Leu
        275                 280                 285

Ala His Val Ala Lys Glu Ser Tyr Leu Glu Ala Arg Leu Val Glu
    290                 295                 300

<210> SEQ ID NO 3
<211> LENGTH: 383
<212> TYPE: DNA
<213> ORGANISM: Corynebacterium glutamicum

<400> SEQUENCE: 3
ttccaatccc tgctgttcac ccttgccccg aaagccatcg cgcgcctgac cgagaaatac      60
ccacacctgc aagtagaaat ctcccaacta gaagtcaccg cagcgctcga agaactccgc     120
gcccgccgcg tcgacgtcgc actcggcgag gaataccccg tggaagtccc ccttgttgag     180
gccagcattc accgcgaagt cctcttcgaa gaccccatgc tgctcgtcac cccagcaagc     240
ggcccatact ctggcctcac cctgccagaa ctccgcgaca tccccatcgc catcgatcca     300
cccgaccttc ccgcgggcga atgggtccat aggctctgcc ggcgcgccgg gtttgagccc     360
cgcgtgacct tgaaaccagc ga                                             383

<210> SEQ ID NO 4
<211> LENGTH: 20
<212> TYPE: DNA
<213> ORGANISM: Artificial Sequence
<220> FEATURE:
<223> OTHER INFORMATION: synthetic DNA

<400> SEQUENCE: 4
ttccaatccc tgctgttcac                                                 20
```

```
<210> SEQ ID NO 5
<211> LENGTH: 20
<212> TYPE: DNA
<213> ORGANISM: Artificial Sequence
<220> FEATURE:
<223> OTHER INFORMATION: synthetic DNA

<400> SEQUENCE: 5
gtgacctttg aaaccagcga                                          20
```